United States Patent
Lee et al.

(10) Patent No.: US 10,996,187 B2
(45) Date of Patent: May 4, 2021

(54) METHOD FOR SIMULTANEOUSLY DETECTING GLUCOSE CONCENTRATION AND PERCENTAGE OF GLYCATED HEMOGLOBIN IN SINGLE TEST STRIP

(71) Applicant: PEACEBIO CO., LTD., Taichung (TW)

(72) Inventors: Cheng-Chih Lee, Taipei (TW); Jen-Lin Chang, Pingtung (TW)

(73) Assignee: PEACEBIO CO., LTD., Taichung (TW)

( * ) Notice: Subject to any disclaimer, the term of this patent is extended or adjusted under 35 U.S.C. 154(b) by 59 days.

(21) Appl. No.: 16/428,578

(22) Filed: May 31, 2019

(65) Prior Publication Data

US 2020/0150074 A1  May 14, 2020

(30) Foreign Application Priority Data

Nov. 14, 2018  (TW) .................................. 107140456

(51) Int. Cl.
| G01N 27/327 | (2006.01) |
| G01N 33/72  | (2006.01) |
| G01N 33/66  | (2006.01) |

(52) U.S. Cl.
CPC ......... *G01N 27/3275* (2013.01); *G01N 33/66* (2013.01); *G01N 33/723* (2013.01); *G01N 27/3278* (2013.01)

(58) Field of Classification Search
CPC .............. G01N 27/327–3272; G01N 27/3278
See application file for complete search history.

(56) References Cited

U.S. PATENT DOCUMENTS

| 5,653,864 A * | 8/1997 | Gotoh ................ G01N 27/3273 |
| | | 204/403.09 |
| 2012/0261257 A1* | 10/2012 | Vanjari .............. G01N 27/3272 |
| | | 204/403.06 |
| 2014/0061044 A1* | 3/2014 | Thekkedath ....... A61B 5/14532 |
| | | 204/403.01 |

FOREIGN PATENT DOCUMENTS

| CN | 101650331 A | 2/2010 |
| EP | 2862584 A1 | 4/2015 |
| TW | 201725284 A | 7/2017 |

OTHER PUBLICATIONS

Defintion of Glucose in the online Encylopedia Britannica, downloaded Sep. 23, 2020 from https://www.britannica.com/science/glucose (Year: 2020).*

Defintion of Glycated hemoglobin in Proteopedia, downloaded on Sep. 23, 2020 from https://proteopedia.org/wiki/index.php/HbA1c_test_for_diabetes (Year: 2020).*

(Continued)

*Primary Examiner* — Alexander S Noguerola
(74) *Attorney, Agent, or Firm* — Merchant & Gould P.C.

(57) ABSTRACT

A test strip includes a working electrode including a conductive layer and an electro-catalytic layer deposited on the conductive layer. A method for simultaneously detecting a glucose concentration and a percentage of glycated hemoglobin in a single test strip includes following steps: providing a blood sample, providing the aforementioned test strip, performing a sample injecting step, performing an initial step, performing a first detecting step, performing a second detecting step, performing a third detecting step, performing a first analyzing step, and performing a second analysis step.

6 Claims, 11 Drawing Sheets

(56) References Cited

OTHER PUBLICATIONS

Cheng et al., "Fabrication of NiOOH/Ni(OH)2@C Electrode for Detecting Blood Glucose by Composited Plating Method," Int. J. Electrochem. Sci. 11 (2016) 6085-6094 (Year: 2016).*
Cherevko et al., "The porous CuO electrode fabricated by hydrogen bubble evolution and its application to highly sensitive non-enzymatic glucose detection," Talanta 80 (2010) 1371-1377 (Year: 2010).*
Zhao et al., "Highly exposed copper oxide supported on three-dimensional porous reduced graphene oxide for non-enzymatic detection of glucose," Electrochmica Acta 176 (2015) 1272-1279 (Year: 2015).*
Song et al., "Nonezymatic Glucose Detection by Using a Three-Dimensionally ordered Macroporous Platinum Template," Chem. Eur. J. 2005, 11, 2177-2182 (Year: 2005).*
Frank Walsh, "The Overall Rates of Electrode Reactions: Faraday's Laws of Electrolysis", Trans. Inst. Metal Finish, 1991, 69(4), 155 (Year: 1991).*

* cited by examiner

METHOD FOR SIMULTANEOUSLY DETECTING GLUCOSE CONCENTRATION AND PERCENTAGE OF GLYCATED HEMOGLOBIN IN SINGLE TEST STRIP

RELATED APPLICATIONS

This application claims priority to Taiwan Application Serial Number 107140456 filed Nov. 14, 2018, which is herein incorporated by reference.

BACKGROUND

Technical Field

The present disclosure relates to a test strip and a method. More particularly, the present disclosure relates to a test strip for detecting glucose concentration and percentage of glycated hemoglobin and a method for simultaneously detecting glucose concentration and percentage of glycated hemoglobin.

Description of Related Art

Diabetes mellitus is a metabolic disease characterized by blood sugar of a patient that is higher than the standard value for a long time. Hyperglycemia can cause symptoms of eating more, drinking more, urinating, and losing weight. Diabetes can be classified into type 1 diabetes, in which the pancreas fails to produce the insulin which is essential for survival, and type 2 diabetes, which results from the body's inability to respond properly to the action of insulin produced by the pancreas. Regardless of the type of diabetes, many complications can occur without treatment. General symptoms of diabetes mellitus include blurred vision, headache, muscle weakness, slow wound healing and itchy skin. Acute complications of diabetes mellitus include diabetic ketoacidemia and hyperglycemic hyperosmolar nonketotic coma. Serious long-term complications of diabetes mellitus include cardiovascular disease, stroke, chronic kidney disease, diabetic foot, and retinopathy. The number of people with diabetes worldwide is 124 million in 1997, and an estimated 422 million adults worldwide suffered from diabetes in 2014.

Under normal circumstances, the diabetes should be determined by the fasting blood glucose level and the percentage of glycated hemoglobin first, and be supplemented by oral glucose tolerance test for further confirmation. The fasting blood glucose level is a blood glucose level measured at least 8 hours after fasting, and refers to the concentration of glucose per 100 grams of plasma in the body when a subject has just got up and has not had breakfast. The oral glucose tolerance test measures blood glucose levels for at least 8 hours after fasting and at least 2 hours after drinking glucose solution. Fasting blood glucose levels and oral glucose tolerance tests can reflect the blood glucose status at the time of blood collection. Glycated hemoglobin (HbA1c) is a form of hemoglobin in the red blood cell that is covalently bound to glucose. When the glucose concentration is higher in the blood, the percentage of glycated hemoglobin (HbA1c) is higher. Once hemoglobin is covalently bound to glucose, it is not easy to unbind until the red blood cells die. The average life span of red blood cells is 120 days, so the detection of glycated hemoglobin in the blood can reflect the average blood glucose level over the past 2-3 months.

Diabetes mellitus and its complications can cause a financial burden and a decline in the quality of life of patients. Therefore, diabetic patients and pre-diabetic patients who have not yet become diabetics urgently need to monitor short-term blood sugar status and long-term blood sugar status to avoid subsequent aggravation or complications. However, the detection of fasting blood glucose level and glycated hemoglobin need to be detected separately, the amount of the blood sample required for the detection of glycated hemoglobin is large, and the reaction process of the detection of glycated hemoglobin is complicated and needs to be operated by professional personnel. Therefore, the conventional method for detecting blood glucose concentration and glycated hemoglobin is inconvenient for the patient, and it is also not easy to monitor the condition of Diabetes mellitus.

SUMMARY

According to one aspect of the present disclosure, a test strip includes a working electrode including a conductive layer and an electro-catalytic layer deposited on the conductive layer. The electro-catalytic layer includes a porous structure, and the electro-catalytic layer is for catalyzing long-chain biomacromolecules or short-chain biomacromolecules in a neutral environment.

According to another aspect of the present disclosure, a method for simultaneously detecting a glucose concentration and a percentage of glycated hemoglobin in a single test strip includes steps as follows. A blood sample is provided. The test strip according to the aforementioned aspect is provided. A sample injecting step is performed, wherein the blood sample is injected into the electro-catalytic layer. An initial step is performed, wherein an initial voltage is provided to the test strip. A first detecting step is performed, wherein a first current signal value of the test strip is obtained at a first detecting potential at a first detection time point. A second detecting step is performed, wherein a background current signal value of the test strip is obtained at a second detecting potential at a second detection time, the second detecting potential is smaller than the first detecting potential, and a potential difference between the second detecting potential and the first detecting potential ranges from 0.05 V to 0.8 V. A third detecting step is performed, wherein a number of electron transfer of the test strip is calculated at the second detecting potential at a third detection time point. A first analyzing step is performed, wherein the first current signal value is compared with a glucose concentration reference data to determine the glucose concentration in the blood sample. A second analysis step is performed, wherein the number of electron transfer is divided by the background current signal value to obtain an electrochemical signal value, and the electrochemical signal value is compared with a glycated hemoglobin percentage reference data to determine the percentage of glycated hemoglobin in the blood sample.

BRIEF DESCRIPTION OF THE DRAWINGS

The present disclosure can be more fully understood by reading the following detailed description of the embodiment, with reference made to the accompanying drawings as follows.

DETAILED DESCRIPTION

A test strip includes a working electrode including a conductive layer and an electro-catalytic layer deposited on the conductive layer is provided. The electro-catalytic layer includes a porous structure, and the electro-catalytic layer is for catalyzing long-chain biomacromolecules or short-chain biomacromolecules in a neutral environment. In more details, the test strip can be a two-electrode system or a three-electrode system. If the test strip is the two-electrode system, the test strip includes the working electrode and a counter/reference electrode. If the test strip is the three-electrode system, the test strip includes the working electrode, a counter electrode, and a reference electrode.

Figure 1:
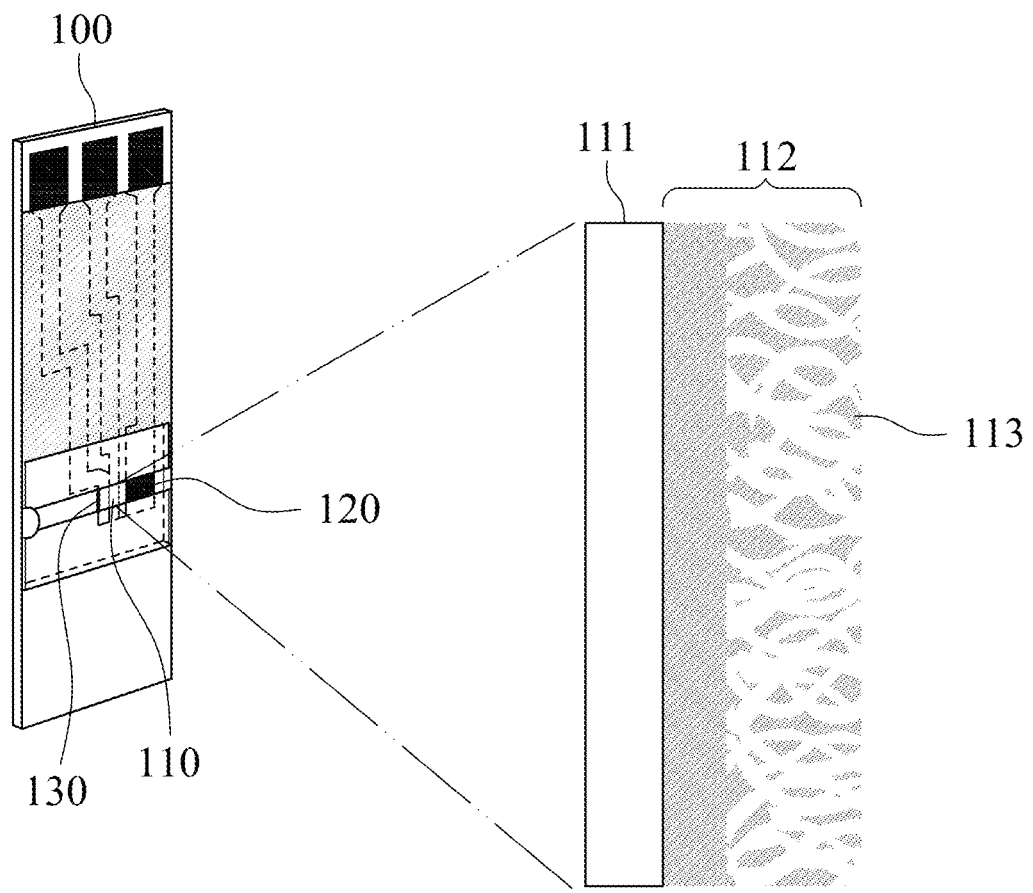
FIG. 1 is a schematic view of a test strip according to one embodiment of the present disclosure.

Please refer to FIG. 1, which is a schematic view of a test strip 100 according to one embodiment of the present disclosure. In the embodiment of FIG. 1, the test strip 100 is the three-electrode system and includes a working electrode 110, a counter electrode 120, and a reference electrode 130.

The working electrode 110 includes a conductive layer 111 and an electro-catalytic layer 112. The working electrode 110 works as an electron donor or an electron acceptor to the analyte with the suitable potential in the electrolyte, and converts the degree of biometric identification or biological action into an electronic signal. It is preferred to use the working electrode 110 with high signal to noise response and wide potential window for electroanalysis. The material of the conductive layer 111 of the working electrode 110 can be composed of a conventional conductive material such as carbon, copper, graphene, platinum, gold, silver or a composite material such as carbon/silver or graphene/platinum.

The electro-catalytic layer 112 is deposited on the conductive layer 111 by chemical modification, and a material of the electro-catalytic layer 112 can be a metal oxide or a metal hydroxide. Preferably, the metal oxide can be $RuO_2$, NiO, CuO or $Al_2O_3$. The metal hydroxide can be $Ru(OH)_2$, NiOOH, CuOOH, $Au(OH)_2$ or PtOH. The electro-catalytic layer 112 includes a porous structure 113, wherein a pore size of the porous structure can range from 200 nm to 400 nm. The electro-catalytic layer 112 is for catalyzing long-chain biomacromolecules or short-chain biomacromolecules in the neutral environment.

The counter electrode 120 plays the opposite role to the working electrode 110. When the working electrode 110 performs an oxidation reaction, the counter electrode 120 performs a reduction reaction, and vice versa. The counter electrode 120 should not participate with the electrochemical reaction except to balance the current observed at the working electrode 110. The common use of the counter electrode 120 is platinum with the characteristic of high stability and the conductivity to accomplish the current path. And the reason why the surface area of the counter electrode 120 is well advised 10 times larger than the surface area of the working electrode 110 is hopefully to catch as much electrons as possible through the counter electrode 120.

The reference electrode 130 is used to control the potential of the working electrode 110, which is kept at a certain potential difference from the working electrode 110 to maintain a stable voltage. The reference electrode 130 has the characteristic of an ideal non-polarized electrode and has a large resistance, allowing only a very small amount of current to pass through to maintain the potential. The reference electrode 130 can be a standard hydrogen electrode (NHE, SHE-Normal Hydrogen Electrode), a saturated calomel electrode (SCE-Saturated Calomel Electrode), a silver/silver chloride electrode (Ag/AgCl-Silver/Silver Chloride Electrode) or a silver oxide electrode.

Figure 2:
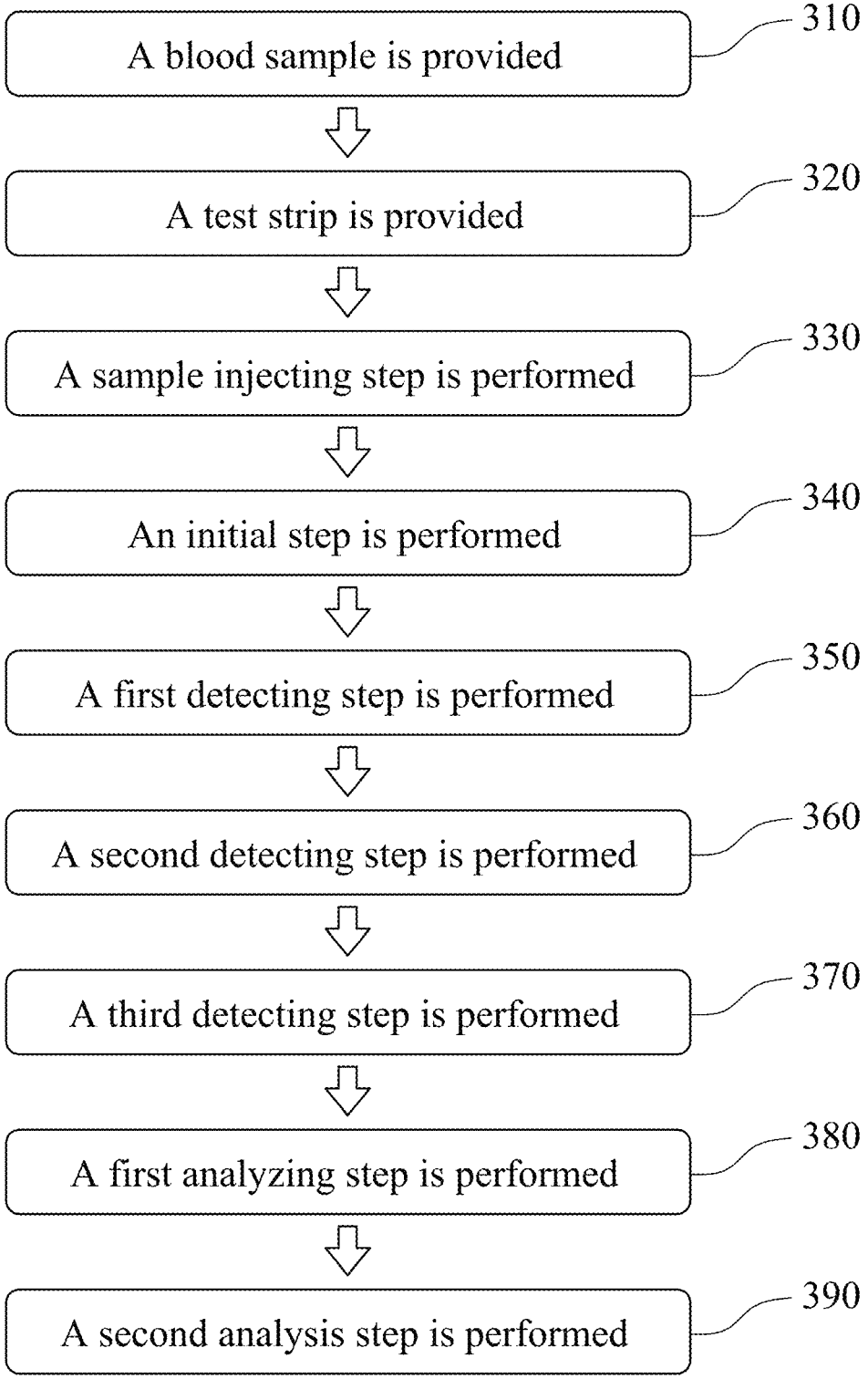
FIG. 2 is a flow diagram showing a method for simultaneously detecting a glucose concentration and a percentage of glycated hemoglobin in a single test strip according to another embodiment of the present disclosure.

Please refer to FIG. 2, which is a flow diagram showing a method for simultaneously detecting a glucose concentration and a percentage of glycated hemoglobin in a single test strip 300 according to another embodiment of the present disclosure. The method for simultaneously detecting the glucose concentration and the percentage of glycated hemoglobin in the single test strip 300 of the present disclosure includes a step 310, a step 320, a sample injecting step 330, an initial step 340, a first detecting step 350, a second detecting step 360, a third detecting step 370, a first analyzing step 380 and a second analysis step 390.

In the step 310, a blood sample is provided. The blood sample is a whole blood sample of a subject, which can be a fresh whole blood sample collected by a blood lancet pen or a blood lancet from a fingertip, or a fresh whole blood sample collected through a blood test.

In the step 320, a test strip is provided. The test strip includes a working electrode including a conductive layer and an electro-catalytic layer. The electro-catalytic layer is deposited on the conductive layer by chemical modification. The electro-catalytic layer includes a porous structure, and the electro-catalytic layer is for catalyzing long-chain biomacromolecules or short-chain biomacromolecules in the neutral environment.

In the sample injecting step 330, the blood sample is injected into the electro-catalytic layer of the test strip. The blood sample can be directly injected into the electro-catalytic layer without a pretreatment step such as centrifugation.

In the initial step 340, a power is coupled to the test strip to provide an initial voltage and electric charge is applied to the glucose, hemoglobin, and glycated hemoglobin to be detected in the blood sample.

In the first detecting step 350, a first current signal value of the test strip is obtained at a first detecting potential at a first detection time point. The first detecting potential is an electrochemical oxidation potential, which can be adjusted according to the material of the electro-catalytic layer of the working electrode, the type of the counter electrolyte, and the scan rate of the analysis parameter.

In the second detecting step 360, a background current signal value of the test strip is obtained at a second detecting potential at a second detection time. The second detecting potential is smaller than the first detecting potential, and a potential difference between the second detecting potential and the first detecting potential ranges from 0.05 V to 0.8 V.

In the third detecting step 370, a number of electron transfer of the test strip is calculated at the second detecting potential at a third detection time point.

The sample injecting step 330, the initial step 340, the first detecting step 350, the second detecting step 360, and the third detecting step 370 are sequentially performed, and a total detection time of the sample injecting step 330 to the third detecting step 370 can be from 10 seconds to 60 seconds. The total detection time is adjusted according to the material of the electro-catalytic layer. The first detection time point can be at 6 to 17 percent of the total detection time after the sample injecting step 330. The second detection time point can be at 23 to 40 percent of the total detection time after the sample injecting step 330. The third detection time point can be at 46 to 66 percent of the total detection time after the sample injecting step 330.

In the first analyzing step 380, the first current signal value is compared with a glucose concentration reference data to determine the glucose concentration in the blood sample.

In the second analysis step 390, the number of electron transfer is divided by the background current signal value to obtain an electrochemical signal value, and the electrochemical signal value is compared with a glycated hemoglobin percentage reference data to determine the percentage of glycated hemoglobin in the blood sample.

The test strip and the method for simultaneously detecting the glucose concentration and the percentage of glycated hemoglobin in the single test strip have been described as mentioned above. In the following, the example will be further provided to illustrate the above-mentioned test strip and the method for simultaneously detecting the glucose concentration and the percentage of glycated hemoglobin in the single test strip. However, the present disclosure is not limited thereto.

EXAMPLE

Figure 3:
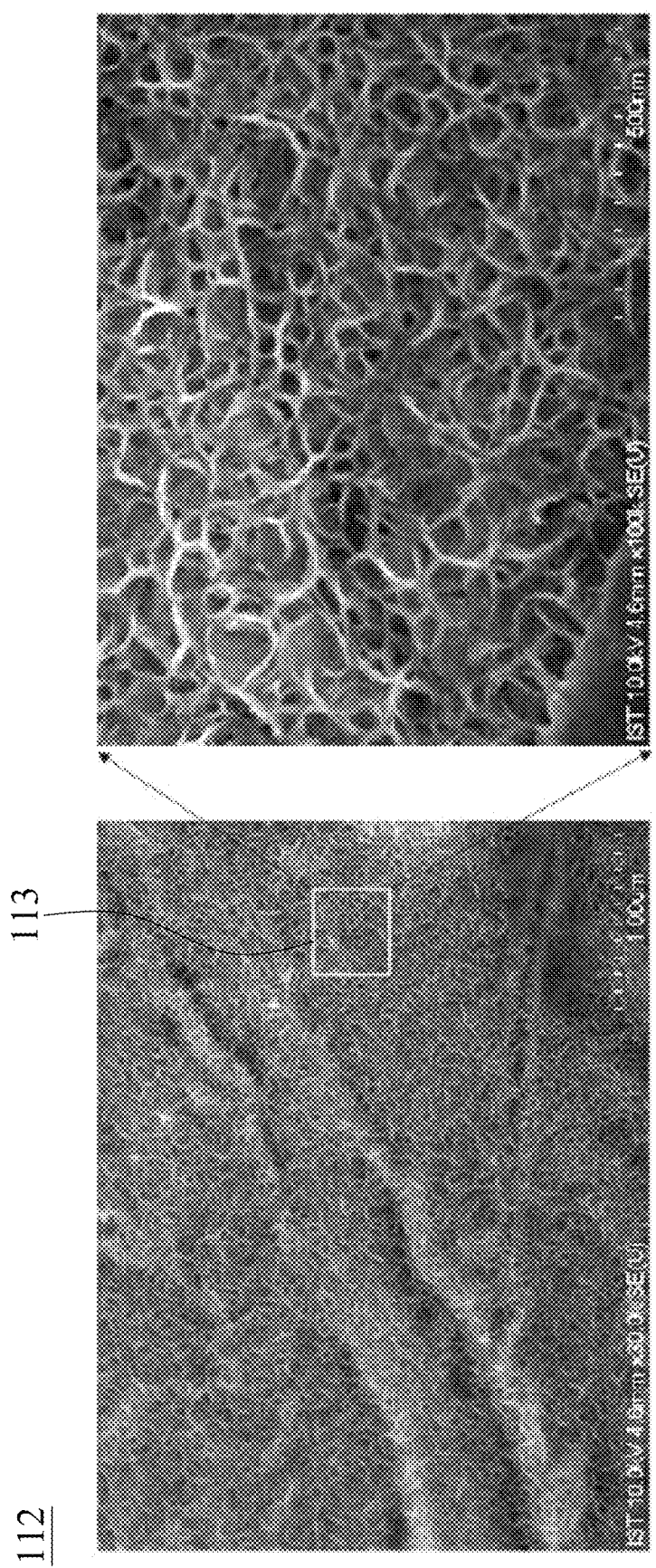
FIG. 3 is a scanning electron microscope image of an electro-catalytic layer of a test strip according to one example of the present disclosure.

As described above, the test strip and the method for simultaneously detecting the glucose concentration and the percentage of glycated hemoglobin in the single test strip are provided. In one example, the test strip is the three-electrode system. Please refer to FIG. 3, which is a scanning electron microscope image of the electro-catalytic layer of a test strip according to one example of the present disclosure. The material of the electro-catalytic layer of the test strip of one example is NiOOH. In FIG. 3, the electro-catalytic layer of the test strip of the example includes a porous structure and is used to catalyze long-chain biomacromolecules or short-chain biomacromolecules in the neutral environment. For example, glucose and glycated hemoglobin can be catalyzed in the neutral environment in the electro-catalytic layer of the test strip of one example. Further, an electrolyte that maintains a neutral or weakly alkaline environment can be used as a counter electrolyte in the example.

Figure 4A:
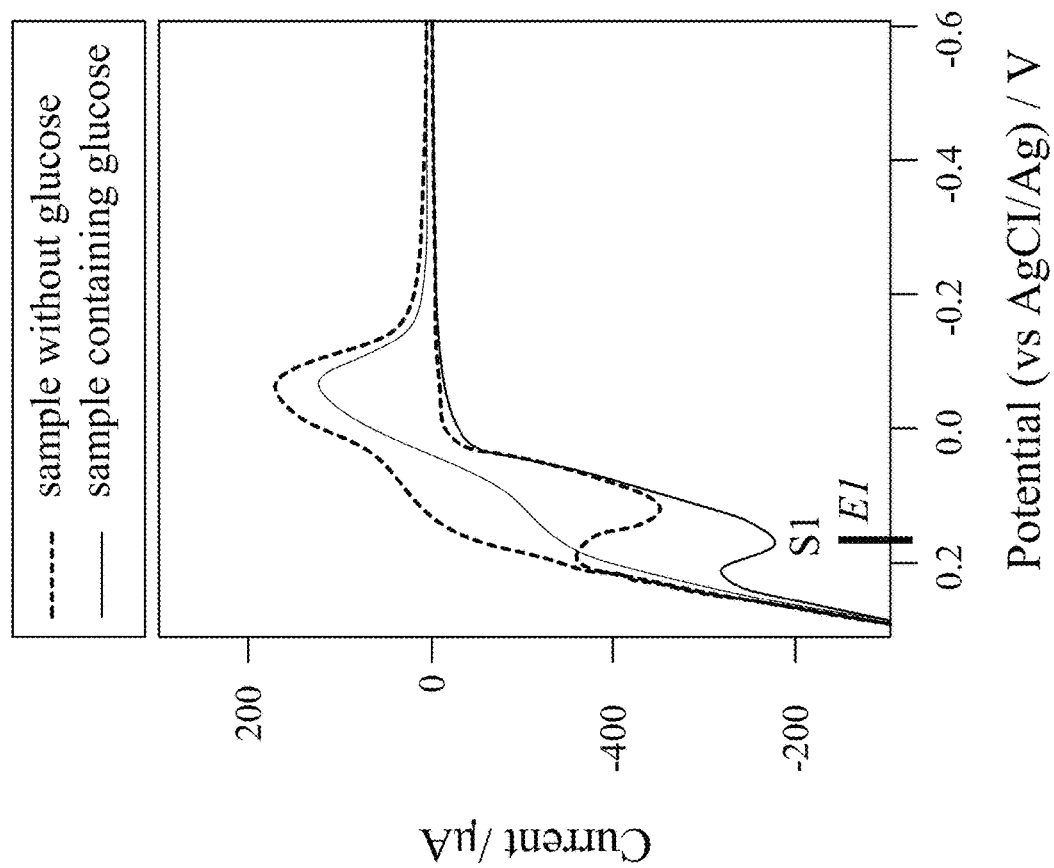
FIG. 4A is a linear sweep voltammogram of the test strip detecting a sample containing glucose according to one example of the present disclosure.

FIG. 4A is a linear sweep voltammogram of the test strip detecting a sample containing glucose according to one example of the present disclosure, wherein the dashed line is a linear sweep voltammogram of the test strip of one example detecting a sample without glucose, and the solid line is a linear sweep voltammogram of the test strip of one example detecting the sample containing glucose. In FIG. 4A, compared with the sample without glucose, the first current signal value S1 can be detected at the first detecting potential E1 when the sample containing glucose is detected by the test strip of one example. The first detecting potential E1 of one example is approximately 0.2 V.

Figure 4B:
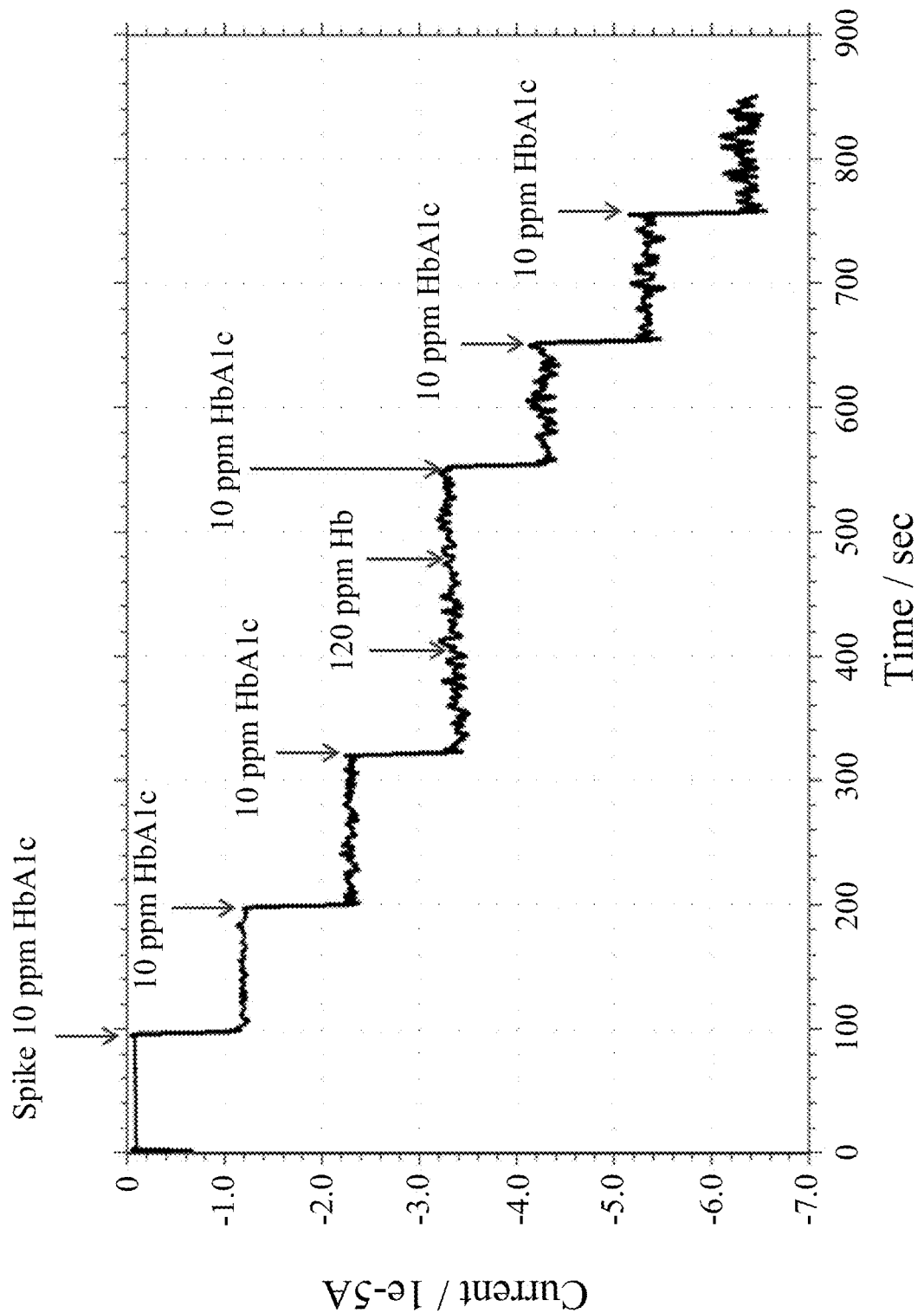
FIG. 4B is a signal graph of current-vs.-time of the test strip detecting a sample containing hemoglobin or a sample containing glycated hemoglobin according to one example of the present disclosure.

FIG. 4B is a signal graph of current-vs.-time of the test strip detecting a sample containing hemoglobin or a sample containing glycated hemoglobin according to one example of the present disclosure, wherein the vertical axis is the current value (unit is ampere, A), and the horizontal axis is the time (in seconds). In FIG. 4B, the sample containing hemoglobin and the sample containing glycated hemoglobin are detected by the test strip of one example at the second detecting potential E2, respectively. The second detecting potential E2 of one example is approximately 0.12 V. In FIG. 4B, when the sample containing hemoglobin is detected by the test strip of one example, the detected current signal value is stable; when the sample containing glycated hemoglobin is detected by the test strip of one example, a change of the current signal value can be detected each time a sample containing glycated hemoglobin (10 ppm) is added. The result indicates that the current signal value detected by the test strip of the present disclosure only changes for glycated hemoglobin and remains stable for hemoglobin. Therefore, the test strip of the present disclosure has the effect of detecting glycated hemoglobin.

Figure 5:
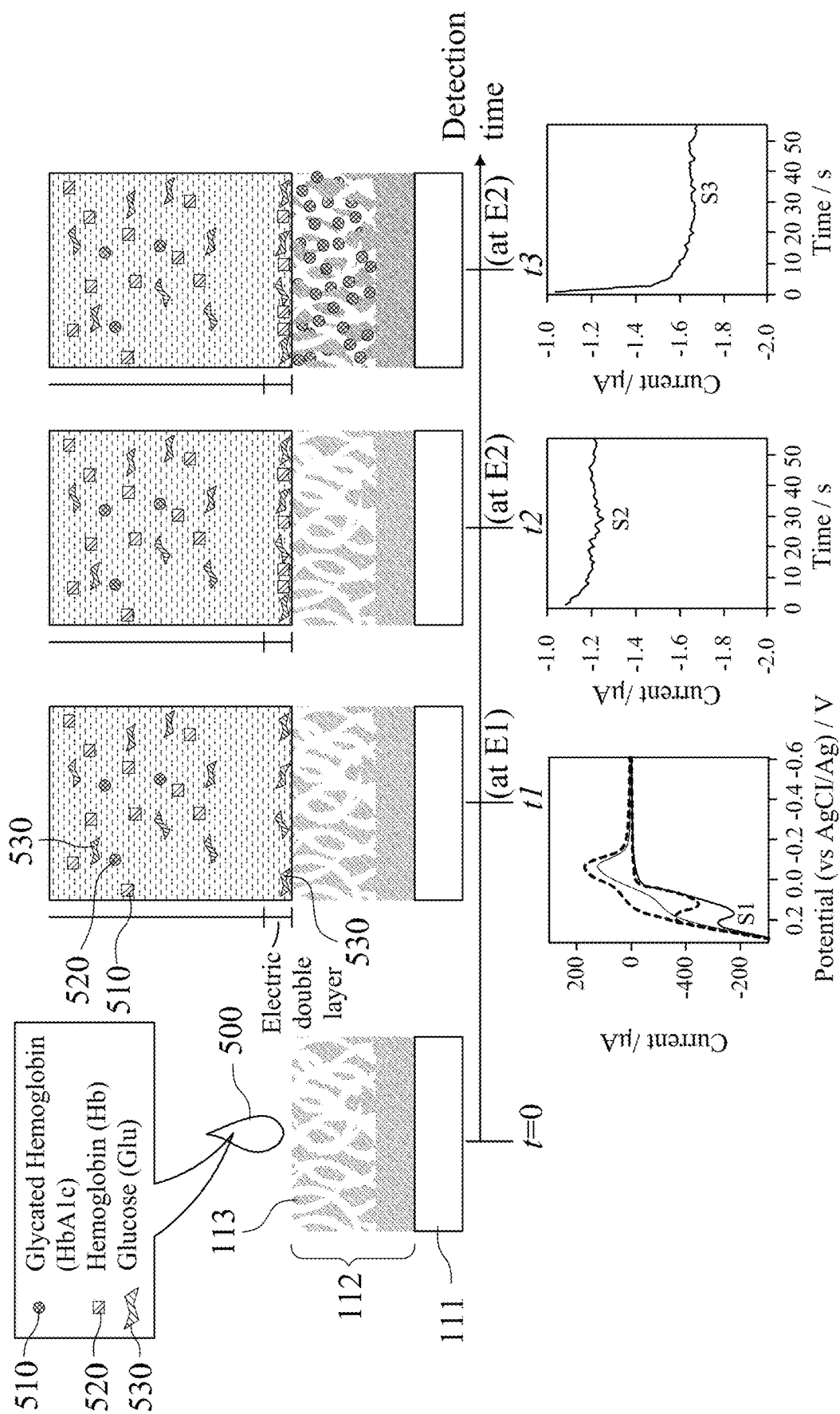
FIG. 5 is a schematic view showing the mechanism of a method for simultaneously detecting a glucose concentration and a percentage of glycated hemoglobin in a single test strip according to another embodiment of the present disclosure.

Please refer to FIG. 5, which is a schematic view showing the mechanism of a method for simultaneously detecting a glucose concentration and a percentage of glycated hemoglobin in a single test strip according to another embodiment of the present disclosure. In FIG. 5, when performing the method for simultaneously detecting the glucose concentration and the percentage of glycated hemoglobin in the single test strip of the present disclosure, the blood sample 500 is injected into the electro-catalytic layer 112 of the test strip 100 at t=0, wherein the blood sample 500 contains glycated hemoglobin 510, hemoglobin 520, and glucose 530. Power is coupled to the test strip of the present disclosure to provide an initial voltage. After a period of time, the glucose 530 in the blood sample 500 is rapidly diffused to the surface of the electro-catalytic layer 112, so that the first current signal value S1 can be detected at the first detecting potential E1 at the first detection time point t1. In one example, the first detection time point t1 is 2 seconds to 10 seconds after the blood sample 500 is injected into the electro-catalytic layer 112, and the first detecting potential E1 is 0.2 V to 0.3 V. After a further period, the hemoglobin 520 in the blood sample 500 is adhered to the surface of the electro-catalytic layer 112. Hemoglobin 520 increases the impedance of the surface of the electro-catalytic layer 112, thereby reducing the detected current signal value. Therefore, the background current signal value S2 can be detected at the second detecting potential E2 at the second detection time point t2. In the example, the second detection time point t2 is 12 seconds to 20 seconds after the blood sample 500 is injected into the electro-catalytic layer 112, and the second detecting potential E2 is 0.12 V to 0.18 V. After a further period, the glycated hemoglobin 510 is adsorbed into the porous structure 113 of the electro-catalytic layer 112, and the number of electron transfer of the test strip of the example is calculated at the third detection time point t3 at the second detecting potential E2. In the example, the third detection time point t3 is 22 seconds to 30 seconds after the blood sample 500 is injected into the electro-catalytic layer 112, the second detection potential E2 is 0.12 V to 0.18 V. The number of electron transfer S3 is calculated by taking the detected redox signal value into formula I, wherein formula I is derived from the current intensity formula and Faraday's law.

$$I \times t = nFN \qquad \text{formula I,}$$

where,
I is current;
t is time;
n is the number of electron transfer;
F is Faraday constant; and
N is mole number.

Further, because the concentration of the glycated hemoglobin 510 in the blood sample 500 is low, the effect of preconcentrating the glycated hemoglobin 510 can be achieved by the mechanism of adsorbing the glycated hemoglobin 510 into the porous structure 113 to improve the detection sensitivity.

Figure 6:
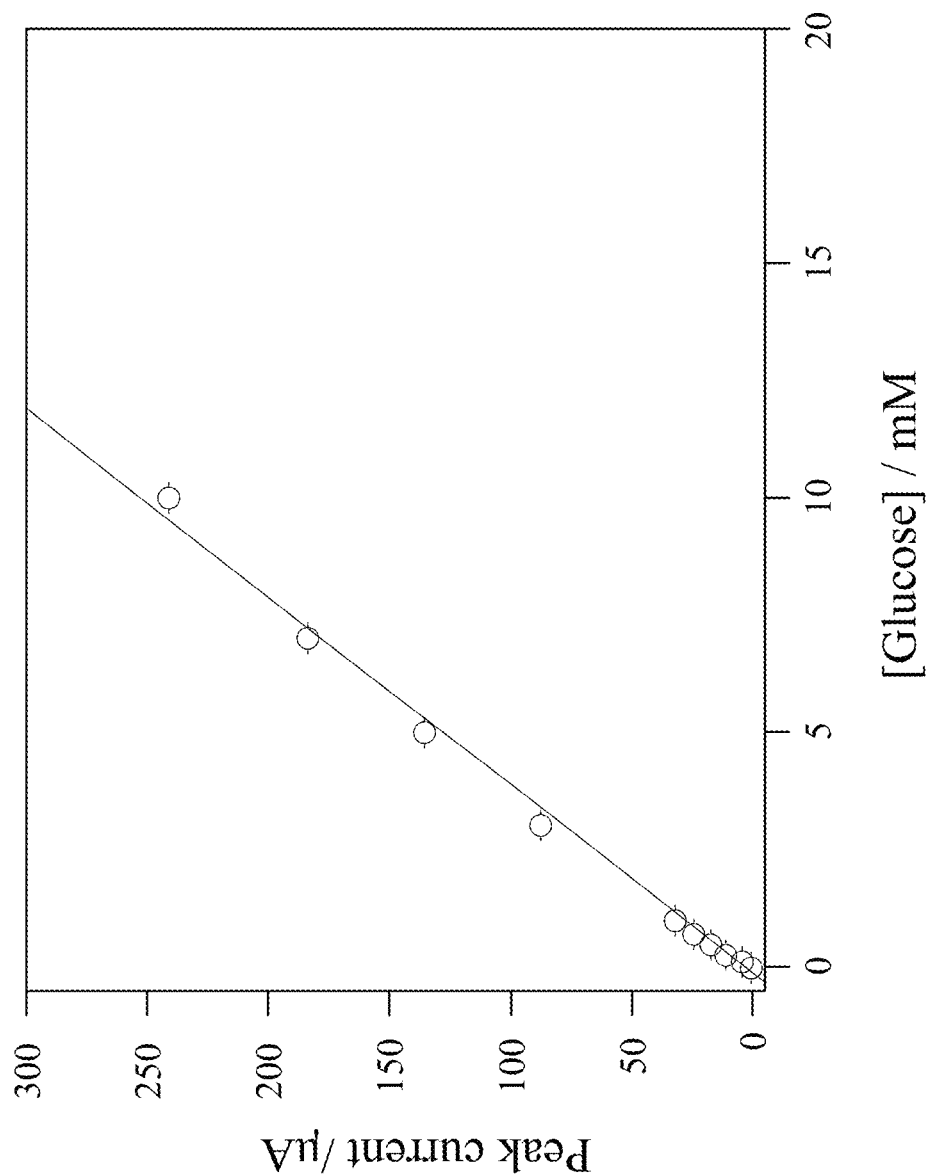
FIG. 6 is a calibration curve of the test strip detecting the sample containing glucose according to one example of the present disclosure.

Then, the first current signal value S1 is compared with a glucose concentration reference data to determine the glucose concentration in the blood sample 500. Please refer to FIG. 6, which is a calibration curve of the test strip detecting the sample containing glucose according to one example of the present disclosure. In FIG. 6, when the sample containing glucose from 0 mM to 20 mM is detected by the test strip of the example, the obtained current signal value shows a good linear relationship with different concentrations of glucose, so it can be used as the glucose concentration reference data. Therefore, the glucose concentration in the blood sample 500 can be determined by comparing the obtained first current signal value S1 with the aforementioned glucose concentration reference data.

Next, the number of electron transfer S3 is divided by the background current signal value S2 to obtain an electrochemical signal value EC, and the electrochemical signal value EC is compared with a glycated hemoglobin percentage reference data to determine the percentage of glycated hemoglobin in the blood sample 500.

Figure 7:
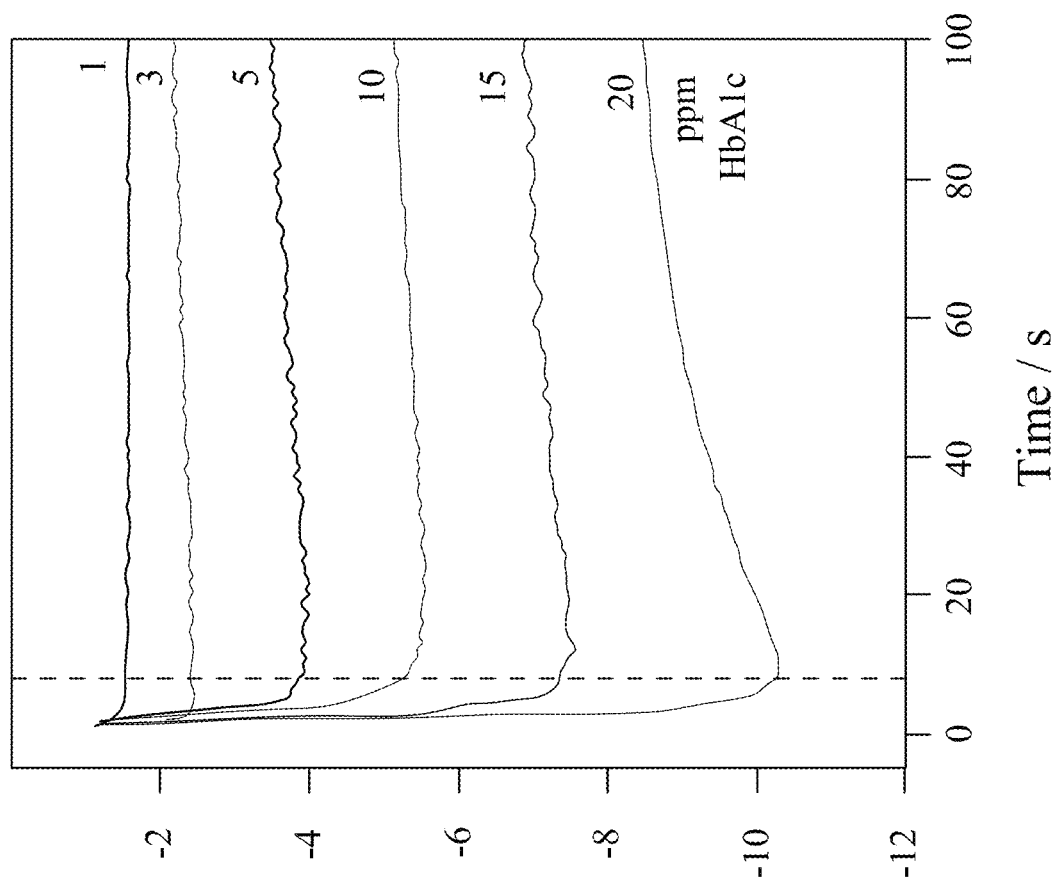
FIG. 7 is a graph of current-vs.-time of the test strip detecting different concentrations of glycated hemoglobin according to one example of the present disclosure.

Please refer to FIG. 7, which is a graph of current-vs.-time of the test strip detecting different concentrations of glycated hemoglobin according to one example of the present disclosure, wherein HbA1c represents glycated hemoglobin. In FIG. 7, when the sample containing glycated hemoglobin from 1 ppm to 20 ppm is detected by the test strip of the example, the obtained current signal value shows a good relationship with different concentrations of glycated hemoglobin, so it can be used as a glycated hemoglobin concentration reference data. A glycated hemoglobin concentration in the blood sample 500 can be determined by comparing the detected redox signal value at the third detection time point t3 with the glycated hemoglobin concentration reference data. Then, the number of electron transfer S3 is calculated using formula 1. The electrochemical signal value EC can be further obtained by dividing the obtained the number of electron transfer S3 by the background current signal value S2.

Figure 8:
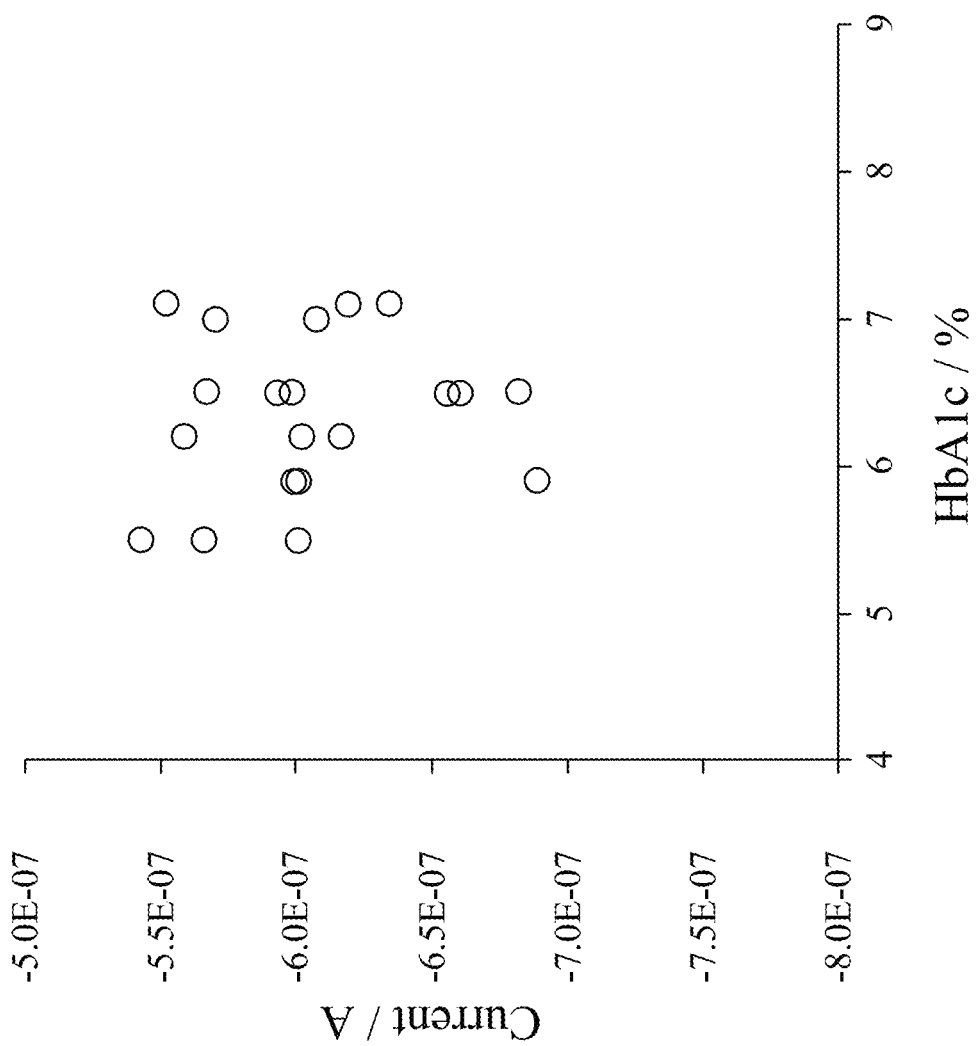
FIG. 8 is a graph showing a relationship between a number of electron transfer and a percentage of glycated hemoglobin measured by a liquid chromatography.
Figure 9:
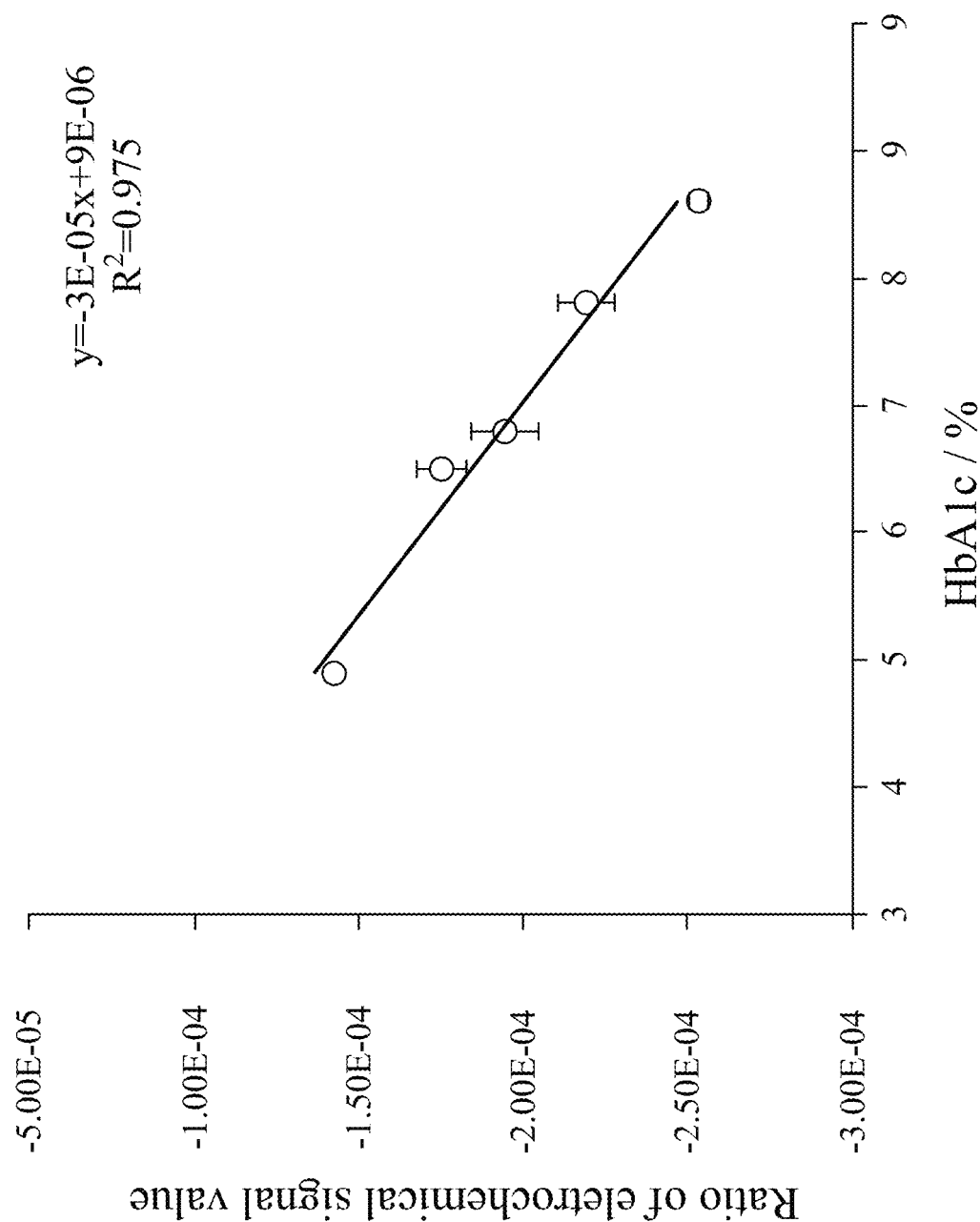
FIG. 9 is a graph showing a relationship between an electrochemical signal value ratio of the present disclosure and the percentage of glycated hemoglobin measured by the liquid chromatography.

Please refer to FIGS. 8 and 9. FIG. 8 is a graph showing a relationship between the number of electron transfer and the percentage of glycated hemoglobin measured by a liquid chromatography, and FIG. 9 is a graph showing a relationship between an electrochemical signal value ratio of the present disclosure and the percentage of glycated hemoglobin measured by the liquid chromatography. The liquid chromatography is the most common method for detecting glycated hemoglobin in the blood sample, and HbA1c represents glycated hemoglobin in FIGS. 8 and 9. In FIG. 8, the number of electron transfer S3 does not have a positive correlation with the percentage of glycated hemoglobin measured by liquid chromatography. However, the electrochemical signal value EC obtained by dividing the number of electron transfer S3 by the background current signal value S2 shows a good linear relationship with the percentage of glycated hemoglobin measured by liquid chromatography, so that it can be used as the glycated hemoglobin percentage reference data. The percentage of glycated hemoglobin in the blood sample 500 can be determined by comparing the obtained electrochemical signal value EC with the glycated hemoglobin percentage reference data.

Figure 10:
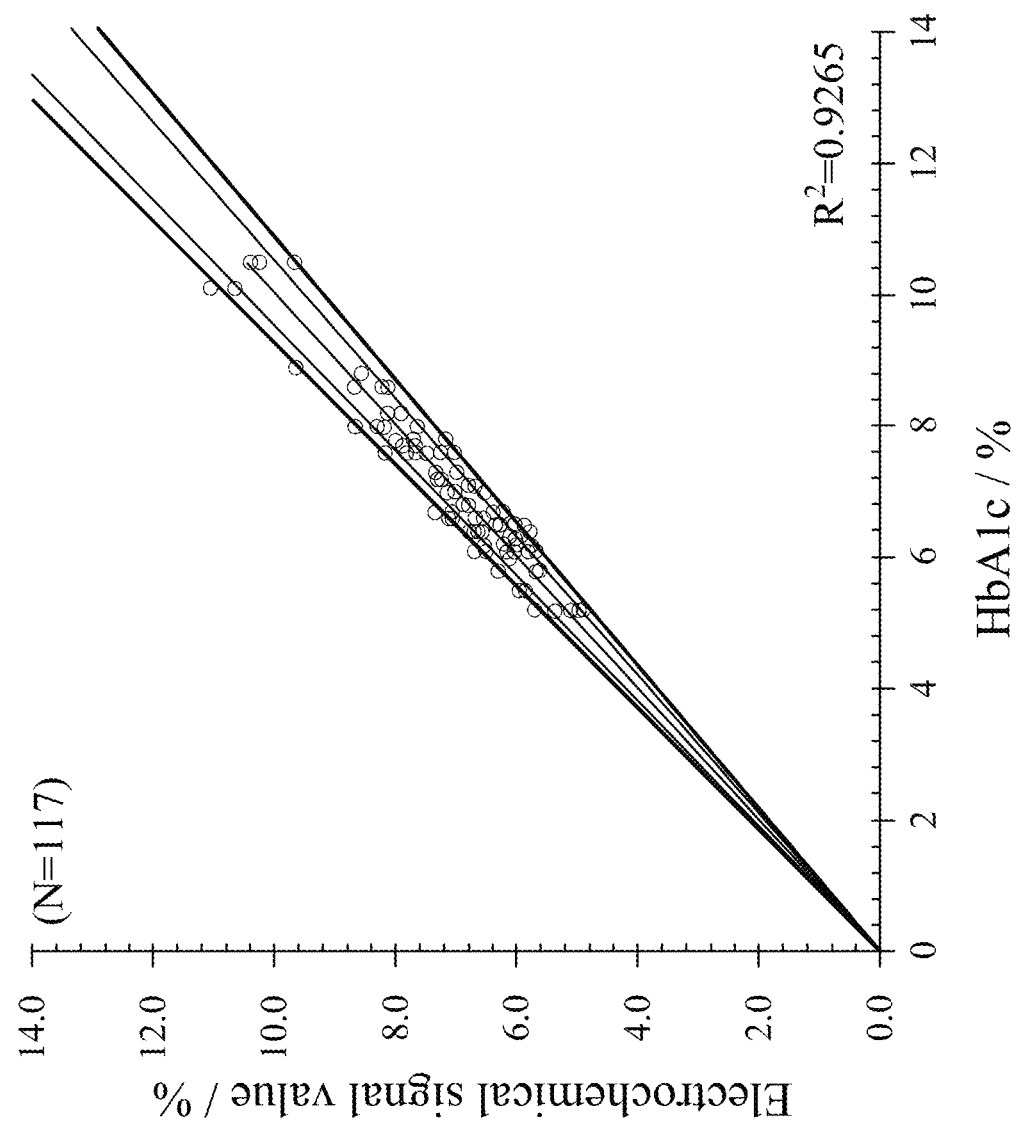
FIG. 10 is a graph showing a relationship between an electrochemical signal value of a blood sample of a subject and the percentage of glycated hemoglobin measured by the liquid chromatography.

Further, the blood samples of 117 subjects are detected by the method for simultaneously detecting the glucose concentration and the percentage of glycated hemoglobin in the single test strip of the present disclosure. Please refer to FIG. 10 and Table 1. FIG. 10 is a graph showing a relationship between an electrochemical signal value of the blood sample of the subject and the percentage of glycated hemoglobin measured by the liquid chromatography, wherein HbA1c represents glycated hemoglobin. Table 1 shows analytical performance of the method for simultaneously detecting the glucose concentration and the percentage of glycated hemoglobin in the single test strip.

TABLE 1

| Characteristic | Performance |
| --- | --- |
| Linear range | 5.2%-10.5% |
| Accuracy | 0.08%-9.96% |
| Precision | 1.24%-5.44% |
| Sample volume | <1.5 μL |
| Analytical time | <30 sec |

In FIG. 10 and Table 1, the electrochemical signal values EC of the blood samples of 117 subjects obtained by the method for simultaneously detecting the glucose concentration and the percentage of glycated hemoglobin in the single test strip of the present disclosure show a good linear relationship with the percentage of glycated hemoglobin measured by the liquid chromatography. Moreover, the method for simultaneously detecting the glucose concentration and the percentage of glycated hemoglobin in the single test strip of the present disclosure has good accuracy in the percentage of glycated hemoglobin of 4%-15% under the condition that the blood sample volume is less than 1.5 μL, and the analysis time is also less than 30 seconds.

To sum up, the blood sample after blood collection can directly injected the test strip of the present disclosure, and then the method for simultaneously detecting a glucose concentration and a percentage of glycated hemoglobin in a single test strip of the present disclosure can be used to accurately and quickly detect the glucose concentration and the percentage of glycated hemoglobin in the blood sample simultaneously. The analysis time of the method for simultaneously detecting a glucose concentration and a percentage of glycated hemoglobin in a single test strip of the present disclosure is less than 30 seconds, and the blood sample does not need the pretreatment step such as centrifugation. Therefore, the test strip and the method for simultaneously detecting a glucose concentration and a percentage of glycated hemoglobin in the single test strip of the present disclosure provide convenience for diabetic patients and pre-diabetic patients to monitor short-term blood glucose status and long-term blood glucose status.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for simultaneously detecting a glucose concentration and a percentage of glycated hemoglobin in a single test strip, comprising:
    providing a blood sample;
    providing a test strip, the test strip comprising:
        a working electrode comprising:
            a conductive layer; and
            an electro-catalytic layer deposited on the conductive layer, wherein the electro-catalytic layer comprises a porous structure;
    performing a sample injecting step, wherein the blood sample is injected into the electro-catalytic layer;
    performing an initial step, wherein an initial voltage is provided to the test strip;
    performing a first detecting step, wherein a first current signal value of the test strip is obtained at a first detecting potential at a first detection time point;
    performing a second detecting step, wherein a background current signal value of the test strip is obtained at a second detecting potential at a second detection time, the second detecting potential is smaller than the first detecting potential, and a potential difference between the second detecting potential and the first detecting potential ranges from 0.05 V to 0.8 V;
    performing a third detecting step, wherein a redox signal value of the test strip is detected at the second detecting potential at a third detection time point;
    performing a first analyzing step, wherein the first current signal value is compared with a glucose concentration reference data to determine the glucose concentration in the blood sample; and
    performing a second analysis step, wherein the redox signal value is compared with a glycated hemoglobin concentration reference data and then calculated a HbA1c signal value, the HbA1c signal value is divided by the background current signal value to obtain an electrochemical signal value, and the electrochemical signal value is compared with a glycated hemoglobin percentage reference data to determine the percentage of glycated hemoglobin in the blood sample.

2. The method for simultaneously detecting the glucose concentration and the percentage of glycated hemoglobin in the single test strip of claim 1, wherein the sample injecting step, the initial step, the first detecting step, the second detecting step, and the third detecting step are sequentially performed, and a total detection time of the sample injecting step to the third detecting step is from 10 seconds to 60 seconds.

3. The method for simultaneously detecting the glucose concentration and the percentage of glycated hemoglobin in the single test strip of claim 1, wherein a material of the electro-catalytic layer is a metal oxide or a metal hydroxide.

4. The method for simultaneously detecting the glucose concentration and the percentage of glycated hemoglobin in the single test strip of claim 3, wherein the metal oxide is $RuO_2$, $NiO$, $CuO$ or $Al_2O_3$.

5. The method for simultaneously detecting the glucose concentration and the percentage of glycated hemoglobin in the single test strip of claim 3, wherein the metal hydroxide is $Ru(OH)_2$, $NiOOH$, $CuOOH$, $Au(OH)_2$ or $PtOH$.

6. The method for simultaneously detecting the glucose concentration and the percentage of glycated hemoglobin in the single test strip of claim 1, wherein a pore size of the porous structure ranges from 200 nm to 400 nm.

* * * * *